(12) United States Patent
Blackledge

(10) Patent No.: US 6,491,646 B1
(45) Date of Patent: Dec. 10, 2002

(54) GUIDEWIRE EXTENSION SYSTEM

(75) Inventor: Victor R. Blackledge, Cologne, MN (US)

(73) Assignee: Lake Region Manufacturing, Inc., Chaska, MN (US)

( * ) Notice: Subject to any disclaimer, the term of this patent is extended or adjusted under 35 U.S.C. 154(b) by 0 days.

(21) Appl. No.: 08/029,748

(22) Filed: Mar. 11, 1993

(51) Int. Cl.$^7$ ................................................. A61B 5/00
(52) U.S. Cl. ...................................................... 600/585
(58) Field of Search ................................. 128/657, 772; 403/164, 165, 221, 296; 604/95, 280

(56) References Cited

U.S. PATENT DOCUMENTS

| | | | |
|---|---|---|---|
| 3,574,373 A | * 4/1971 | Derf | ........................... 403/296 |
| 4,827,941 A | 5/1989 | Taylor et al. | |
| 4,846,193 A | 7/1989 | Tremulis et al. | |
| 4,875,489 A | 10/1989 | Messner et al. | |
| 4,922,923 A | 5/1990 | Gambale | |
| 4,966,163 A | 10/1990 | Kraus | |
| 5,101,213 A | 3/1992 | Harada | |
| 5,113,872 A | 5/1992 | Jahrmarkt et al. | |
| 5,117,838 A | 6/1992 | Palmer et al. | |
| 5,234,002 A | * 8/1993 | Chan | ........................... 128/772 |
| 5,271,415 A | * 12/1993 | Foerster et al. | ............. 128/772 |

FOREIGN PATENT DOCUMENTS

| | | | |
|---|---|---|---|
| EP | 0383159 A1 | 8/1990 | |
| GB | 572089 | * 9/1945 | ................. 403/296 |

OTHER PUBLICATIONS

Pamphlet describing the CINCH guidewire extension systems of Cordis Corporation, Jan. 1991.

* cited by examiner

Primary Examiner—Max Hindenburg
(74) Attorney, Agent, or Firm—Michael Best & Friedrich LLP; Grady J. Frenchick

(57) ABSTRACT

A roll-formed, guidewire extension system for connecting an extension wire to a guidewire is disclosed. The system comprises a connector or sleeve, such as a turnbuckle, having a tubular outer body, a guidewire retention means, an extension wire retention means, a guidewire and an extension wire. A sleeve or turnbuckle nut is produced by rolling a portion of a formable hollow tubular workpiece upon an elongated projection with the projection being disposed at an angle with respect to the axis of the workpiece. This process is repeated on the remaining part of the workpiece to create external threads in the sleeve of opposite pitch. The roll-formed external beads or dents in the sleeve create threads in the interior of the sleeve, the threads running in opposite directions and meeting at approximately the middle of the sleeve. The guidewire and the extension wire engagement means are preferably helically wound wires which are connected e.g., brazed to reduced diameter portions of the guidewire/extension wire. The guidewire is connected to the extension wire by inserting the respective engagement portions into the open ends of the sleeve, and rotating the sleeve in a single direction. In a preferred practice the turnbuckle sleeve, is rotatively affixed to one or the other of the extension wires or guidewires, preferably the extension wire.

12 Claims, 4 Drawing Sheets

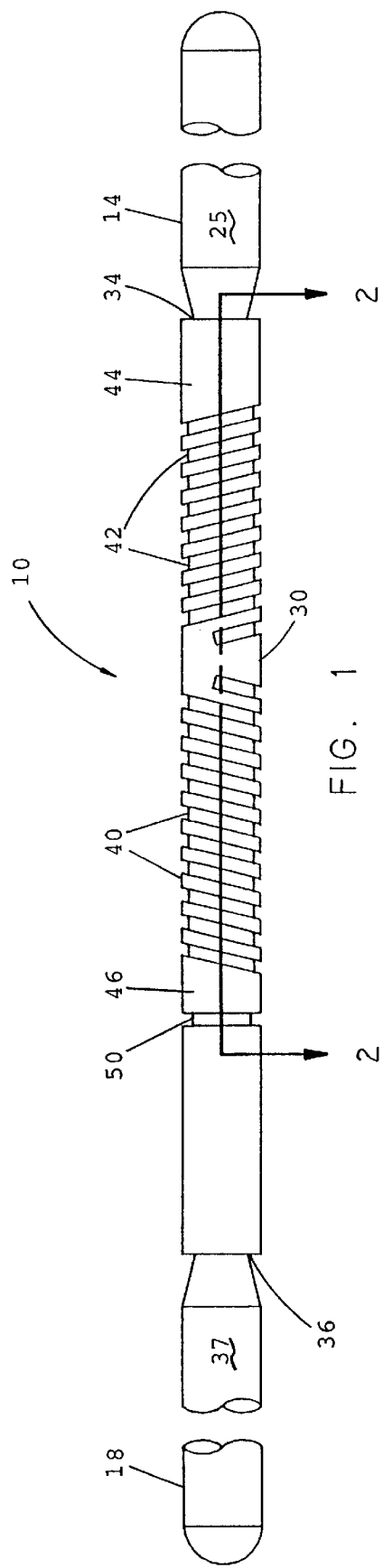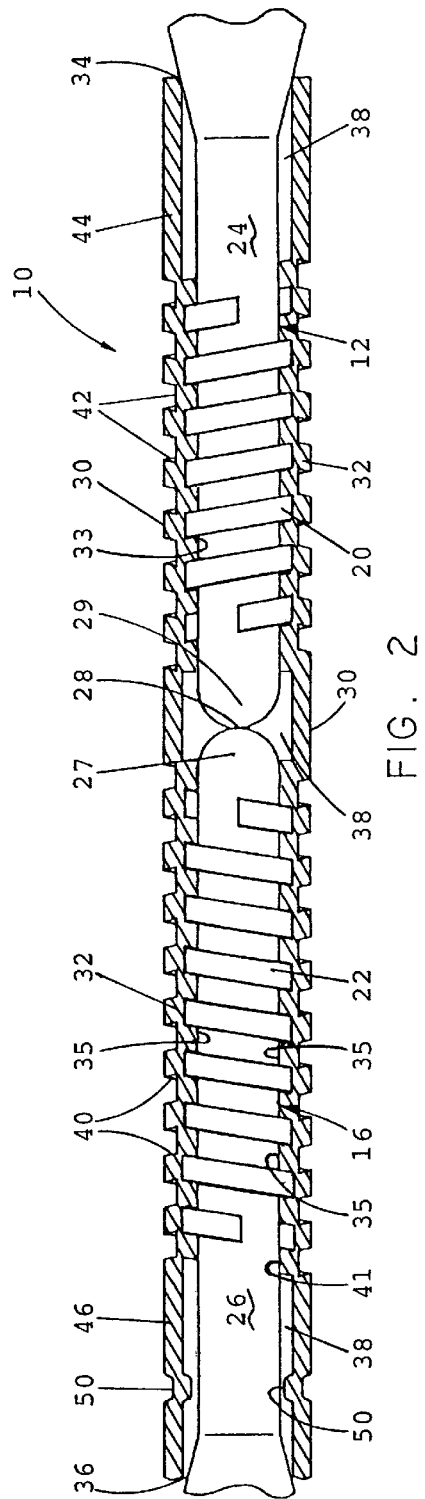

GUIDEWIRE EXTENSION SYSTEM

FIELD OF THE INVENTION

The present invention relates in general to the field of guidewires. Guidewires are used to position catheters in exploratory procedures, diagnosis, and treatment of various medical conditions. More particularly, this invention relates to a guidewire extension system for connecting or coupling a guidewire, primary or initial wire to an extension or secondary wire during a medical procedure.

BACKGROUND OF THE INVENTION

Guidewires are used in various medical procedures to position medical devices at desired locations within a patient's vascular system. Guidewires, which are steerable, are inserted and maneuvered through the patient's vasculature to a previously chosen location. Once in place, the guidewire provides the means to place a non-steerable device, such as a catheter, at the chosen body site. For example, a catheter is slid over the guidewire until the catheter, or some working portion thereof, is positioned within the vasculature at the desired location. Generally speaking, guidewires of a standard length are longer than the non-steerable devices with which they are used to permit independent movement of the device and the wire.

Angioplasty is one surgical application where a guidewire is often used. In angioplasty a dilatation catheter having an inflatable balloon structure is used to compress occlusive or blockage material against the sides of a vessel, thereby permitting (ideally) circulation to be reestablished. In preparatory procedures, the site of a vascular restriction, occlusion or stenosis is identified. The guidewire is inserted into the patient's femoral artery and maneuvered or steered to the location of the restriction. Insertion of the guidewire is facilitated by an video X-ray device which allows the surgeon to observe the movement of the guidewire's distal tip. The guidewire distal tip generally comprises a radiopaque metal to enhance X-ray viewing. A dilatation catheter then is inserted over the guidewire so that its working segment is located adjacent the restriction. Generally this means that the catheter balloon is positioned adjacent the vascular restriction or blockage.

During a simple angioplasty procedure, the dilatation catheter balloon is inflated to open the restriction, and then is removed along with the guidewire. However, complications sometimes arise which prevent the surgeon from completing this simple procedure. Occasionally the balloon catheter malfunctions. Sometimes a larger (or smaller) balloon is required further to dilate the vascular restriction, or another device or other type of catheter is needed to remove vascular material. For whatever the reason, the guidewire extension system of this invention is used when the catheter, or other such device, has to be removed and replaced with another device or catheter.

In the usual procedure to exchange catheters, the guidewire is removed from the patient leaving the catheter in the vascular system. An exchange wire is inserted through the catheter and the catheter removed, leaving the exchange wire in place. . The new catheter is inserted over the exchange wire and the exchange wire removed and replaced with the guidewire.

It is desirable to keep the guidewire in the patient's vasculative for various reasons. However, the primary reason for not removing the guidewire is that the initial placement of the guidewire requires extensive, time consuming, manipulation. Removal and repositioning of the guidewire would be equally time consuming, possibly requiring further exposure to drugs, exposure to additional radiation, and, in general, infliction of additional trauma to the patient.

In those cases where catheter exchange is desired, the surgeon could simply remove the catheter over the guidewire, leaving the guidewire in the patient. However, to facilitate the removal and replacement of a catheter, the guidewire must be sufficiently long to allow the surgeon to grip a portion of the wire as the catheter is being withdrawn. This requires the guidewire to be long enough to provide an external portion longer than the catheter in addition to the portion remaining in the patient.

Unfortunately, a guidewire of sufficient length has inferior handling characteristics, thereby making more difficult the steering and maneuvering manipulations needed for guidewire placement. The added length also imposes itself on the usually cramped surgical arena thereby causing distractions to other surgical support activities. It is for these reasons that guidewires are usually only slightly longer than balloon catheters, e.g. 20–50 centimeters longer, and that a much longer exchange wire (and exchange procedure) is used. In other words, the guide wire-extension wire combination has a length approximating that of an exchange wire. Illustrating the above, a dilatation catheter has a length in the range of about 130 cm to about 160 cm, a suitable guidewire would have a length in the range of about 160 cm to about 200 cm and an exchange wire would have a length in the range of about 260 cm to about 340 cm. As can be imagined from the above, utilization of an exchange wire in an exchange wire procedure is complicated and time consuming. This invention simplifies catheter exchange and eliminates the need to use an exchange wire.

A recent development involves coupling or connecting a second length of wire, sometimes called an extension wire or secondary wire, to the exposed, proximal end of a guidewire. The second wire length should be of sufficient length to allow the catheter to be withdrawn while leaving the guidewire in the patient. Various approaches have been suggested for effecting the attachment of an extension wire to a guidewire.

In one approach, such as that described in U.S. Pat. No. 4,922,923 to Gambale et al., a guide wire and an extension are joined together by crimping. A special crimping tool is disclosed in the Gambale et al., '923 patent. A drawback of this approach is that once the wires have been crimped, the connection therebetween is substantially permanent, and the extension wire cannot be detached from the guidewire except by severing it, e.g., by cutting.

Instead of crimping the guidewire to the extension wire, attempts have been made to engage the extension wire to the guidewire frictionally. Such attempts are described, for example, in U.S. Pat. No. 5,113,872 to Jahrmarkt et al., and related U.S. Pat. No. 5,117,838 to Palmer et al. These two patents disclose a guidewire extension system in which the distal end of the extension wire comprises a small diameter tube in which there is disposed a small diameter, open pitch, flat wire coiled spring. The proximal end of the guidewire has a reduced diameter portion which is inserted into the tube assembly to complete the connection. The reduced diameter proximal end of the guidewire is slightly larger than the internal diameter of the coiled spring of the extension wire, thereby creating a frictional engagement when one is inserted into the other. Palmer et al. disclose the utilization a swivel joint for minimizing twisting of the extension guidewire when connecting or disconnecting it from the extension wire. A device as described in these two patents would be very difficult to manufacture reliably and apparently requires an alignment tool to ease insertion.

U.S. Pat. No. 4,875,489 to Messner et al., discloses an extendable guidewire in which concentric tubular segments are secured to one or the other of the sections to be connected. The inner tubular segment has a longitudinal slot therein which permits it to expand when a cooperating male portion is inserted therein. The outer tubular member of the connector assembly restricts the expansion of the inner tubular member as the male portion is inserted therein.

U.S. Pat. No. 4,846,193 to Tremulis et al., disclose a guidewire having first and second telescopically extendable sections movable between axially extended and retracted positions. No disengagement of the guidewire and extension wire is disclosed.

U.S. Pat. No. 4,966,136 to Kraus et al., discloses an internally threaded female connection member secured to the distal end of the extension wire. The internally threaded female connection member is disclosed to be freely rotatable with respect to the extension wire by securement thereto by means of a collar. The body of the extension wire has a distal enlargement which cooperates with the collar to permit it to be freely rotated. The female connection member of the extension wire cooperates with a threaded male portion located on the proximal end of the guidewire. The mechanism disclosed by Kraus et al., however, sacrifices pushability and flexibility as the ball and socket joint do not effect a mechanical lock sufficiently to transmit such desirable properties.

U.S. Pat. No. 4,827,941 to Taylor et al. discloses a guidewire extension system employing a tubular female connector portion on one wire and a cooperating male portion on the other. The connecting male portion has an effective diameter in one radial dimension which is slightly larger than the inner diameter of the tubular portion. In a preferred practice, the male end portion of the Taylor et al. guidewire has an undulating shape, which, when inserted into the tube creates an interference fit.

The guidewire extension systems discussed above all have drawbacks. Either they have not provided easy engagement or they have disengaged too easily. While frictional engagement overcomes the disadvantages of crimping, disengagement may occur. Problems of kinking at the connection have been experienced with some systems. Moreover, prior extendable wires for use in coronary angioplasty procedures have been found to be unsuitable in peripheral arteries because the connections are not strong enough. Further, some connections have larger diameters than the rest of the guidewire system. This may cause snagging of the catheter. It also means that the catheter with which such connection system is used must have a larger internal diameter than would be necessary were a smaller diameter coupler employed.

Accordingly, a principal object of the present invention is to provide a threaded-type guidewire extension system which is reliable, easy to use and easy to manufacture.

It is a further object of the present invention to provide a guidewire extension system which minimizes the possibility of system failure by kinking or undesirable bending at the connection between the guidewire and the extension wire.

Another object of the present invention is to provide a guidewire extension system utilizing what is referred to as a turnbuckle configuration which does not require that either the guidewire or extension wire be rotated when attaching one to the other. It is advantageous that the guidewire be held stationary because the guidewire is located within the patient's blood vessel where. unnecessary movement can induce trauma. It is also advantageous to have the majority of the length of the extension wire held stationary during the connection process. Having the extension wire self-contained in its tubular carrier package allows medical personnel to concentrate upon engaging the two wires. An uncontained extension wire is awkward, and thus complicates the process of effecting a guidewire/extension wire union during a medical procedure.

It is still a further object of the present invention to provide a guidewire extension system which has substantially the same flexibility and pushability at its connection as that of the remainder of the length of the guidewire.

It is yet another object of the present invention to provide a unitized guidewire extension system having a uniform, smooth, continuous outer diameter along the guidewire, connector, and extension wire. Methods of manufacturing an extension system of this invention and methods of using a system of this invention also are disclosed.

BRIEF SUMMARY OF THE INVENTION

Briefly, in one aspect, the present invention is an extension system for rotatively connecting the proximal end of a guidewire to the distal end of an extension wire. In accordance with the present invention, the system comprises engagement means, such as threads located on the proximal end, and distal end, respectively, of a guidewire and an extension wire. The system further includes a cylindrical sleeve, coupler, or connector, the connector having a deformable wall or body wall. The deformable body wall defines openings on each end of the connector and a cavity extending between the openings. The body wall further defines oppositely pitched, exteriorly-formed, interior threads. The oppositely-pitched, interior threads extend toward the center of the connector. In one embodiment, the interior threads run the entire length of the connector body and meet at approximately the middle. In a preferred practice, the externally-formed internal threads begin at a point interiorly disposed from the openings. This leaves a segment of the body wall which is substantially smooth between the sleeve openings and the start of the thread. The threads are adapted to cooperate with the respective engagement means of the guidewire and extension wire so that the engagement means are retained within the sleeve.

The system further comprises means for rotatively retaining the connector on one or the other of the guidewire or extension wire. In one embodiment, this retention means comprises an annular bead or dent in the sleeve. The annular bead is of sufficient width so that it will not pass over threads on the guidewire or extension wire on which it is located. Thus the guidewire and extension wire may be connected or coupled by inserting the engagement means into the connector and rotating the connector in a single direction.

In a method of making the present extension system, the externally-formed, internal thread is roll formed by rolling a deformable, suitably thin walled, sleeve material over an elongate protuberance, skin or projection from an otherwise substantially flat surface. The sleeve, which has an axis, is rolled over the projection at an angle with respect to its axis with sufficient force to deform the connector body create therein a substantially continuous, external bead or dent. The sleeve body is sufficiently thin so that rolling the sleeve body over the shim creates an internal, helical thread according to the invention. Having rolled the sleeve in one direction to create an internal thread of a first pitch, the process is repeated, starting adjacent the remaining end of the sleeve, to create the second oppositely pitched thread. In a further embodiment, the oppositely pitched threads could be created in a single step by rolling the deformable sleeve, with sufficient force, in one direction over two obliquely angled (i.e., defining an open "V"), elongate shims.

BRIEF DESCRIPTION OF THE DRAWINGS

Thus there is shown in the attached Figures and described in the foregoing Detailed Description illustrative embodiments of the present invention wherein like numerals are used to designate like features and wherein:

FIG. 1 is a side perspective view of one embodiment of the present invention;

FIG. 2 is a longitudinal sectioned view of the embodiment of the invention shown in FIG. 1 taken along lone 2—2;

DETAILED DESCRIPTION OF THE INVENTION

Figure 3:
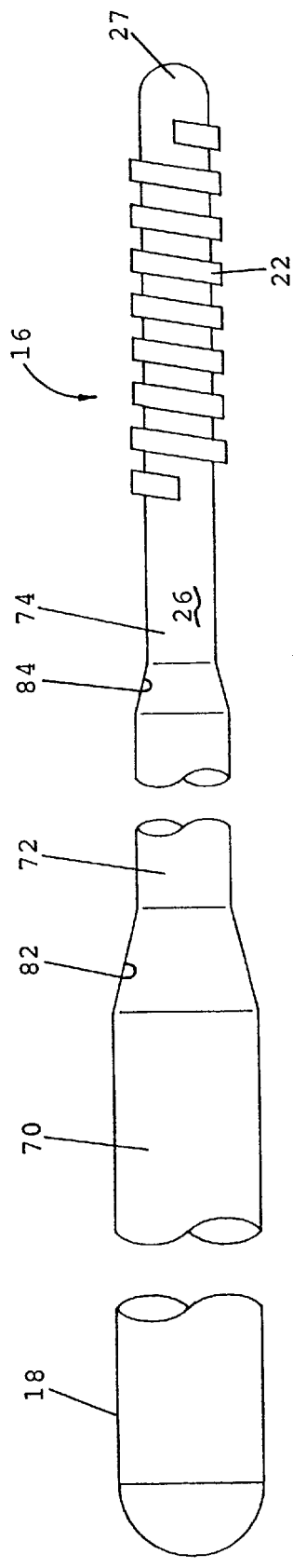
FIG. 3 is a side elevational view of the proximal end of an extension wire useable in a practice of this invention.

Discussions of the techniques of using guidewires for the purpose of guiding a catheter to the site of a catheterization process are included in many issued patents. Such patents have also included discussions of the catheterization procedure itself and of techniques for retaining extension wire within tubular transportation and dispensing assemblies. The discussion of these issues at column 2, lines 64–68, all of column 3 and column 4, lines 1–33 (and the associated FIGS.) of the above-referenced Palmer et al. '838 patent is pertinent to this invention. The entirety of that teaching from the Palmer et al. '838 patent is incorporated by reference herein.

In accordance with one aspect of the present invention, there is shown in FIGS. 1–2 a guidewire extension system 10. Guidewire extension system 10 comprises engagement means 12 located on the proximal end of guidewire 14, and engagement means 16 located on the distal end of extension wire 18. In this embodiment of the invention, the engagement means on the respective ends of the guidewire and extension wire are oppositely wound helical threads 20, 22. Threads 20, 22 are located on a reduced diameter segments 24, 26 (i.e., reduced from the diameter of the longer, main portions 25, 37) of the respective wires. Threads 20, 22 may be created by, for example, brazing a coil spring to the reduced diameter distal/proximal segments of the respective wires. Utilization of reduced diameter distal/proximal portions on the respective wires is important because this reduces the overall diameter or profile of the connection system thereby reducing the required size of the passage of any device passing thereover. Also as shown in FIG. 2, the distal and proximal engagement means or segments of the respective wires means abut each other (at 28). The abutting ends of the respective wires are hemispherically configured 27,29 to minimize frictional engagement. It is preferred to hemispherically configured ends 27, 29 not actually touch each other. In other words, it is preferred for hemispherical ends 27, 29 not to be in contact with each other and thereby leave a space within sleeve 30. It is important, however, that the inside wall of opening 34 be in contact with shoulder or taper 86 (shown in FIG. 4) when the guidewire and extension wire are finally coupled.

The system further includes a cylindrical connector, coupler, or sleeve 30. Sleeve or connector 30 has a deformable body wall 32. Body wall 32 defines openings 34,36 in each end and a cavity 38 extending therebetween. Body wall 32 also defines oppositely pitched interior threads 33, 35. Oppositely pitched threads 33, 35 are formed e.g., by rolling, an external bead or thread 40, 42 in deformable body wall 32. Thread 40,42 may oppositely traverse the entire length of body wall 32 or, as shown, they may begin interiorly of openings 34, 36 leaving a portion 44, 46, of body wall 32, substantially smooth. Processes for creating bead or threads 40, 42 (and simultaneously threads 33, 35) in sleeve 30 are further discussed below.

Extension system 10 further includes means for rotatively retaining connector or sleeve 30 on one or the other of the guidewire or the extension wire. In the embodiment shown, the retention means comprises a radial or annular bead or dent 50. Annular bead 50 is intentionally created to be too wide to fit between adjacent helices of thread 22, and thereby retains sleeve 30 on extension wire distal end 26. Bead 50 is sized so that sleeve 30 can be rotated about extension wire 18 without detaching sleeve 30 therefrom. Bead 50 also is annular or radial as opposed to the helical configuration of thread 22. This disparity in cooperative relationship (or non-cooperation) prevents bead 50 from following thread 22 during the connection/disconnection process. Obviously, the distance between bead 50 and the start of thread 40 (at 41) must be sufficiently long so as to permit the guidewire and extension wire to abut if that is the design preference (at 28) without being restricted in their longitudinal movement i.e., before bottoming out. It is merely a matter of design preference whether sleeve 30 is rotatively retained on the guidewire or the extension wire. Preferably, sleeve 30 is retained on the extension wire distal end portion as shown.

Figure 4:
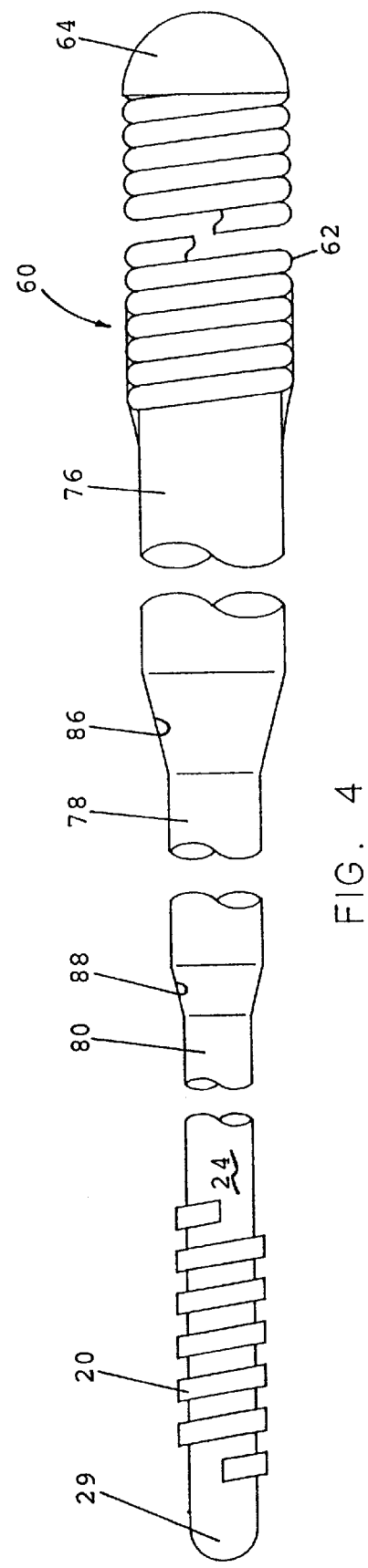
FIG. 4 is a side elevational view of the distal end of an guidewire useable in a practice of this invention.

FIGS. 3 and 4 show extension wire distal portions, and guidewire proximal portions, respectively. FIG. 4 also shows the distal end 60 of the guidewire. Distal guidewire end 60 has a coil spring 62 thereabout and terminates in an atraumatic tip 64. As is shown in these FIGS. The guidewire or the extension wires each may have a plurality of diameters (indicated at portions 70, 72, 74 and 76, 78, 80, respectively) coupled by tapers 82, 84 and 86, 88, respectively. As is well known in this art, the guidewire body or the extension wire body can be provided with segments or portions having different diameters or tapers so as to enhance steerability and flexibility. Portions of either or both wires may be coated to enhance lubricity, abrasion resistance and for other conventional purposes.

Figure 6:
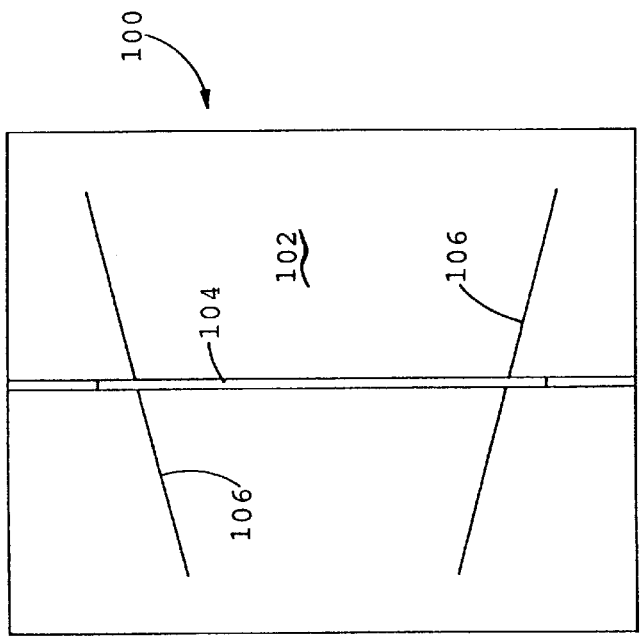
FIG. 6 is a top view of the tool of FIG. 5.
Figure 5:
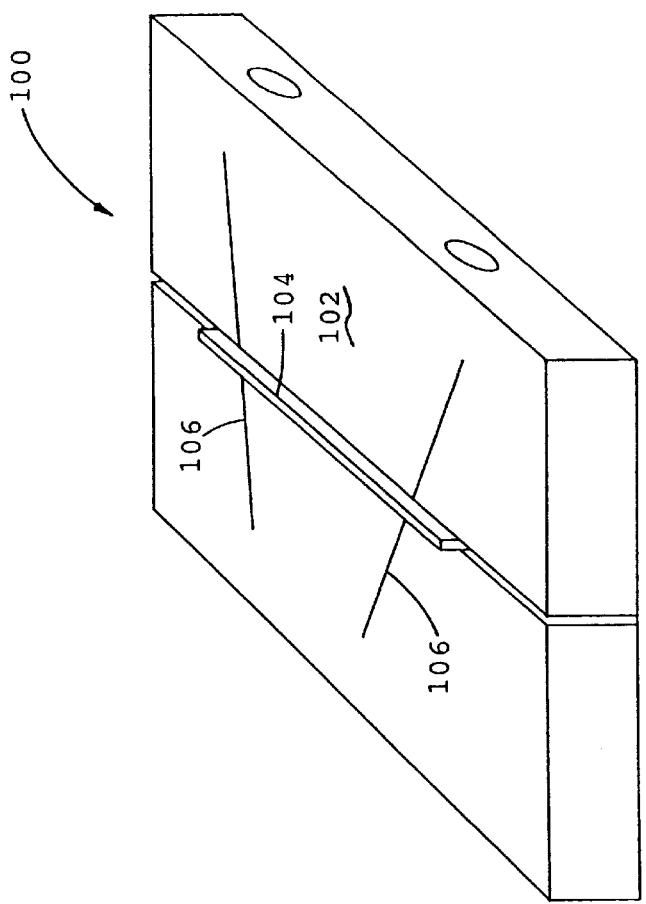
FIG. 5 is a side elevational view of a roll forming jig or tool used to make turnbuckles of the present invention.

FIGS. 5 and 6 illustrate a jig, tool or guide 100, which could be used to make a sleeve of the present invention. As is shown, the jig 100 comprises a substantially flat surface 102 having an elongate protuberance 104 upwardly projecting therefrom. Protuberance projects above surface 102 a distance such that when a deformable sleeve is rolled thereover, an external bead or thread is created therein. For example, protuberance 104 could rise above surface 102 a distance of 0.002 in to about 0.004 inches. Lines 106 have been drawn or scored on surface 102 to indicate the position of a sleeve which is to be roll-formed in accordance with the invention. A sleeve (not shown) is placed so that its axis is parallel with line 106 on one end of protuberance 104. The sleeve then is rolled against protuberance 104 while maintaining its axis parallel to line 106 but obliquely angled with respect to the edge of protuberance 104. The sleeve is rolled with sufficient force so that a helical external bead or dent is created in the sleeve. This, in turn, creates an internal helical thread which can be used to connect a guidewire to an extension wire. The process then is repeated starting on the opposite or remaining end of the sleeve to create an oppositely wound, externally-formed, internal thread. If two obliquely angled protuberances or shims were employed in an open "V" configuration, both threads could be impressed in the sleeve in a single rolling step. Simultaneous creation of two external beads obviously will require application of increased rolling force.

As can be seen the thickness of the wall must be chosen so that the external bead or dent creates an interior thread of suitable height. For example, a wall thickness in the range of about 0.002 to about 0.004 inches (and thicker) has been found to be workable. Thicker walled cylindrical workpieces theoretically could be employed if sufficient rolling force can be applied to create the bead thread. Coupler materials which are suitably deformable when they have a thickness in the range described above include, stainless steel, e.g., 304 v stainless steel, copper, bronze or brass. Stainless steel is preferred because of its relative inertness.

It has been found that one technique for monitoring the roll-forming process to assure accurate placement of the sleeve and sufficient depth of the thread is to roll the sleeve against the protuberance under a flat, transparent sheet. A transparent sheet is placed on top of the sleeve, the appropriate angle (between the axis of the sleeve and the line protuberance) identified and maintained, the force monitored, and the threaded sleeve created by observing the sleeve through the transparent sheet while rolling it against the protuberance. This substantially manual process may be automated in accordance with known techniques.

The wall 32 of the outer body may be tapered or flared at each end 34, 36 to provide easy insertion of the extension and guidewire segments. Alternatively, the ends of the body may be (and usually are) formed square for ease of manufacture while still allowing solid engagement between the ends of the body and the extension and guidewires.

Alternatively, a helical path or locus (instead of a continuous thread) may be formed on the inside wall of the tubular outer body by creating a locus of divots or bumps in the outside of the tubular outer body. This creates a locus of bumps, dimples, or other projections inside of the tubular outer body which are functionally equivalent to an interior thread. In addition to roll forming, threads may be exteriorly formed within the tubular outer body by other means such as machining or by molding. All such equivalent formation techniques are within the methodology of the present invention.

The guidewire 14 and extension wire 18 are preferably constructed of stainless steel or other metal. Radiopaque metals, and shape memory alloys e.g., Nitinbl may be employed. Generally, the wires have diameters in the range of about 0.010 inches to about 0.018 inches, but may have diameters up to 0.038 inches.

To create threads 20, 22, helically wound wires may be attached to the extension core of the guidewire and extension wire by welding, soldering, adhesives, or frictional engagements, for example. Additionally, engagement means may also be created by forming threads or other engagement means on the respective extrusion cores by roll forming or, other conventional means. A suitable distal end/proximal end bulbous enlargement could be substituted for the above-described threads.

Figure 7:
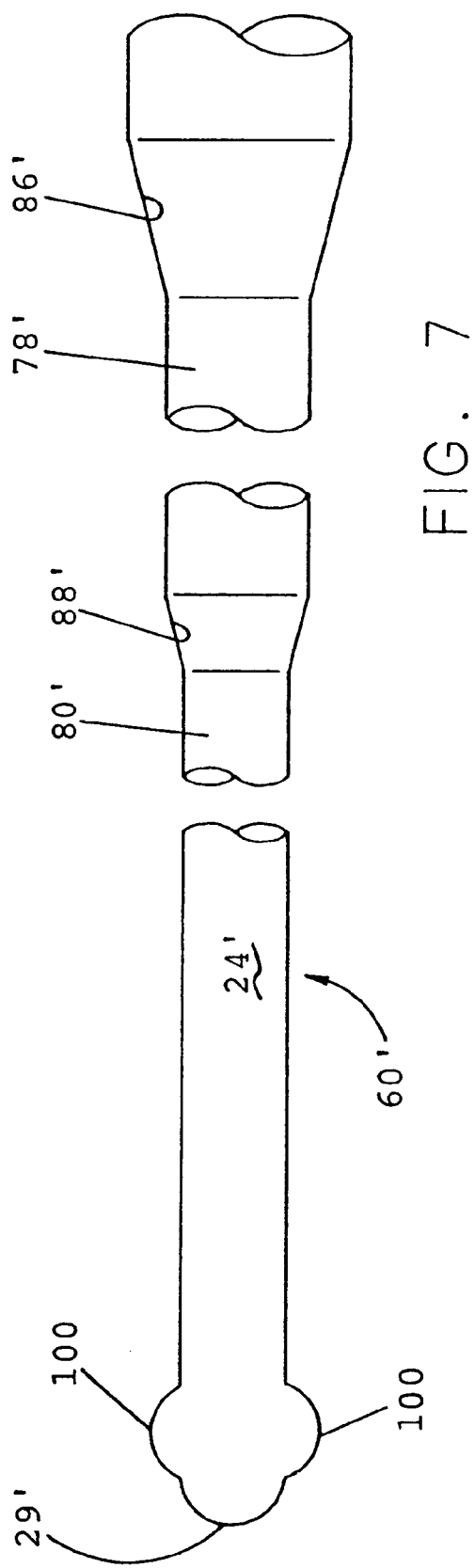
"FIG. 7 is a side view of another embodiment of the present invention."

FIG. 7 illustrates this feature with enlargement 100 being disposed on the proximal end of, e.g., a guidewire 60'. The guidewire proximal end is otherwise substantially the same as that shown in FIG. 4, the primes being used to show that similarity. Enlargement 100 engages oppositely pitched interior threads 30 to provide the couple. Threads are particularly preferred because they provide the most reliable connection.

The guidewire extension system described herein provides many advantages. Connecting the guidewire and the extension wire by the use of this system is advantageous since there is little possibility for disengagement of the exterior or extension wire from the guidewire during normal use. Moreover, the guidewire extension wire connection is made without the need to rotate either the guidewire or the extension wire. The attachment juncture is sufficiently strong to produce approximately the same flexibility and pushability as the guidewire and extension wire would exhibit were they a single piece. Further, the attachment juncture provides a unitized system that has a smooth, substantially continuous outer diameter or profile of the extension wire, guidewire, and outer body. The smooth, continuous outer diameter of the attachment structure prevents snagging of the catheter on the guidewire or the coupler system and permits use of a catheter having the minimum diameter necessary to achieve the desired results.

While a particular form of the invention has been illustrated and described, it will be apparent that various modifications can be made without departing from the spirit and scope of the invention. Accordingly, it is not intended that the invention be limited to the specific embodiment disclosed in the drawings and described in detail hereinabove.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is as follows:

1. An extension system for rotatively connecting a proximal end of a guidewire to a distal end of an extension wire, the system comprising:
    a) engagement means located on the proximal end of the guidewire;
    b) engagement means on the distal end of the extension wire;
    c) a cylindrical connector, the connector having a deformable body wall which defines:
        i) openings in each end of the connector;
        ii) a cavity extending between the openings;
        iii) oppositely pitched, exteriorly formed interior threads, the threads running at least a portion of the distance between said openings, the threads being adapted to cooperate with the respective engagement means of the guidewire and the extension wire so as to retain said engagement means within said connector;
    d) means for retaining the connector on one or the other of said guidewire or said extension wire, said means permitting said connector to be rotated with respect to the wire on which it is retained, whereby the guidewire engagement means and the extension wire engagement means may be coupled by inserting either of said engagement means into said connector and rotating said connector in a single direction.

2. A system according to claim 1 wherein the engagement means on the guidewire comprises a bulbous enlargement.

3. A system according to claim 1 wherein the engagement means on the guidewire comprises a thread disposed on a reduced diameter proximal segment of the guidewire.

4. A system according to claim 1 wherein the means for retaining the connector comprises an annular bead on one end of the connector and a helical thread located on the extension wire, the bead and thread being uncooperatively sized.

5. A system according to claim 1 wherein the exteriorly formed thread is roll-formed.

6. A system according to claim 1 wherein the oppositely pitched threads defined by the wall run substantially the entire length of the connector and meet at approximately its middle.

7. A system according to claim 1 wherein the oppositely pitched threads are disposed inward from the openings leaving a portion of the wall immediately adjacent the openings which is substantially smooth.

8. A method for coupling an engagement means of a guidewire and an engagement means of an extension wire comprising the steps of:

providing a guidewire having an engagement means;

providing an extension wire having an engagement means;

providing a thin-walled, deformable, hollow, cylindrical sleeve having an axis, openings in each end and a longitudinal cavity therethrough;

providing a substantially flat surface having disposed thereon an upwardly projecting elongate protuberance;

rolling the sleeve over the protuberance at an angle with respect to said axis to create in said wall a first external bead and correspondingly an internal thread of a first pitch;

rolling the sleeve over the protuberance a second time, at an angle with respect to said axis, in a direction opposite that of the first rolling step so as to create therein a second external bead and correspondingly an internal thread of a second pitch;

coupling the guidewire and extension wire means by, inserting said engagement means of said guidewire and said extension wire into said openings of said sleeve, and rotating said sleeve in a single direction so that said guidewire and extension wire engagement portions engage the internal threads of the sleeve and are simultaneously pulled toward each other from opposite directions and thereby become mechanically engaged.

9. A method according to claim 8 wherein the guidewire engagement means comprises a helical coil which has been bonded to a reduced diameter proximal portion of the guidewire to create a thread.

10. A method according to claim 8 wherein the extension wire engagement portion comprises a helical coil which has been attached to a reduced diameter distal portion of the extension wire to create a thread.

11. A method according to claim 8 which further comprises the step of affixing the sleeve to one of the guidewire or the extension wire so that said sleeve may be rotated with respect thereto.

12. A method according to claim 11 wherein the affixing step is accomplished by inserting the sleeve over the extension wire or guidewire engagement means and roll forming an annular bead in the sleeve adjacent one end of the sleeve, said bead being disposed substantially perpendicularly to the axis of the sleeve and being located between the opening and an external bead.

* * * * *